United States Patent
Baum et al.

(10) Patent No.: US 8,690,951 B2
(45) Date of Patent: Apr. 8, 2014

(54) BASE PLATFORM FOR AN ARTIFICIAL JOINT

(75) Inventors: Ines Baum, Bollschweil (DE); Markus Rauscher, Steckborn (CH); Peter Wendt, Dahlikon (CH)

(73) Assignee: Zimmer, GmbH, Winterthur (CH)

( * ) Notice: Subject to any disclaimer, the term of this patent is extended or adjusted under 35 U.S.C. 154(b) by 119 days.

(21) Appl. No.: 12/093,855

(22) PCT Filed: Jan. 17, 2006

(86) PCT No.: PCT/EP2006/000370
§ 371 (c)(1),
(2), (4) Date: Jun. 2, 2008

(87) PCT Pub. No.: WO2007/057054
PCT Pub. Date: May 24, 2007

(65) Prior Publication Data
US 2008/0294268 A1    Nov. 27, 2008

(30) Foreign Application Priority Data
Nov. 18, 2005  (EP) .................................. 05025291

(51) Int. Cl.
*A61F 2/40* (2006.01)
*A61F 2/30* (2006.01)

(52) U.S. Cl.
USPC ...................................... 623/19.11; 623/18.11

(58) Field of Classification Search
USPC .............. 623/19.11–19.14, 22.36–22.38
See application file for complete search history.

(56) References Cited

U.S. PATENT DOCUMENTS

| | | | |
|---|---|---|---|
| 2,725,878 | A | 12/1955 | Reiter |
| 3,815,157 | A | 6/1974 | Skorecki et al. |
| 3,842,442 | A | 10/1974 | Kolbel |
| 3,869,730 | A | 3/1975 | Skobel |
| 3,916,451 | A | 11/1975 | Buechel et al. |
| 3,978,528 | A | 9/1976 | Crep |
| 4,030,143 | A | 6/1977 | Elloy et al. |
| 4,040,131 | A | 8/1977 | Gristina |
| 4,206,517 | A | 6/1980 | Pappas et al. |
| 4,318,316 | A | 3/1982 | Guilliams |
| 4,608,052 | A | 8/1986 | Van Kampen et al. |

(Continued)

FOREIGN PATENT DOCUMENTS

| | | |
|---|---|---|
| AU | 714659 | 10/1996 |
| CA | 2216955 | 2/2004 |

(Continued)

OTHER PUBLICATIONS

Katz et al. Machine Translation of FR 2776506A1.*

(Continued)

*Primary Examiner* — Marcia Hoffman
(74) *Attorney, Agent, or Firm* — Schwegman, Lundberg & Woessner, P.A.

(57) ABSTRACT

The invention relates to a base platform (11) for an artificial joint, in particular for an artificial shoulder joint, wherein the platform can be anchored on the bone and serves as a support for an artificial joint component (15, 17) that can be provided both in the form of a shell component (15) for an anatomical configuration and also in the form of a ball component (17) for an inverse configuration, and wherein different joint components can be mounted on the platform.

19 Claims, 8 Drawing Sheets

(56) References Cited

U.S. PATENT DOCUMENTS

| | | |
|---|---|---|
| 4,645,450 A | 2/1987 | West |
| 4,664,668 A | 5/1987 | Beck et al. |
| 4,693,723 A | 9/1987 | Gabard |
| 4,778,469 A | 10/1988 | Lin et al. |
| 4,863,474 A | 9/1989 | Brown et al. |
| 4,919,669 A | 4/1990 | Lannelongue |
| 4,936,853 A | 6/1990 | Fabian |
| 4,938,769 A | 7/1990 | Shaw |
| 4,963,155 A | 10/1990 | Lazzeri et al. |
| 4,964,865 A | 10/1990 | Burkhead et al. |
| 5,007,931 A | 4/1991 | Smith |
| 5,020,519 A | 6/1991 | Hayes et al. |
| 5,080,673 A | 1/1992 | Burkhead et al. |
| 5,133,764 A | 7/1992 | Pappas et al. |
| 5,147,407 A | 9/1992 | Taeger |
| 5,275,601 A | 1/1994 | Gogolewski et al. |
| 5,290,313 A | 3/1994 | Heldreth |
| 5,308,357 A | 5/1994 | Lichtman |
| 5,314,479 A | 5/1994 | Rockwood, Jr. et al. |
| 5,326,354 A | 7/1994 | Kwarteng |
| 5,358,526 A | 10/1994 | Tornier |
| 5,361,782 A | 11/1994 | Bauer |
| 5,364,397 A | 11/1994 | Hayes et al. |
| 5,405,398 A | 4/1995 | Buford, III |
| 5,413,605 A | 5/1995 | Ashby et al. |
| 5,429,639 A | 7/1995 | Judet |
| 5,462,563 A | 10/1995 | Shearer et al. |
| 5,520,690 A | 5/1996 | Errico et al. |
| 5,531,746 A | 7/1996 | Errico et al. |
| 5,534,027 A | 7/1996 | Hodorek |
| 5,549,682 A | 8/1996 | Roy |
| 5,571,202 A | 11/1996 | Mathys, Sr. et al. |
| 5,607,426 A | 3/1997 | Ralph et al. |
| 5,609,641 A | 3/1997 | Johnson |
| 5,609,645 A | 3/1997 | Vinciguerra |
| 5,643,265 A | 7/1997 | Errico et al. |
| 5,647,873 A | 7/1997 | Errico et al. |
| 5,669,911 A | 9/1997 | Errico et al. |
| 5,674,225 A | 10/1997 | Muller |
| 5,690,630 A | 11/1997 | Errico et al. |
| 5,702,457 A | 12/1997 | Walch et al. |
| 5,702,486 A | 12/1997 | Craig et al. |
| 5,723,018 A | 3/1998 | Cyprien et al. |
| 5,725,588 A | 3/1998 | Errico et al. |
| 5,732,992 A | 3/1998 | Mauldin |
| 5,814,097 A | 9/1998 | Sterman et al. |
| 5,817,094 A | 10/1998 | Errico et al. |
| 5,849,015 A | 12/1998 | Haywood et al. |
| 5,871,548 A * | 2/1999 | Sanders et al. ............ 623/22.36 |
| 5,876,402 A | 3/1999 | Errico et al. |
| 5,888,204 A | 3/1999 | Ralph et al. |
| 5,944,723 A | 8/1999 | Colleran et al. |
| 5,976,147 A | 11/1999 | Lasalle |
| 6,045,582 A | 4/2000 | Prybyla |
| 6,110,179 A | 8/2000 | Flivik et al. |
| 6,113,605 A | 9/2000 | Storer |
| 6,139,550 A | 10/2000 | Michelson |
| 6,159,217 A | 12/2000 | Robie et al. |
| 6,197,063 B1 | 3/2001 | Dews |
| 6,206,925 B1 | 3/2001 | Tornie |
| 6,210,444 B1 | 4/2001 | Webster et al. |
| 6,214,052 B1 | 4/2001 | Burkinshaw |
| 6,228,120 B1 | 5/2001 | Leonard et al. |
| 6,238,435 B1 | 5/2001 | Meulink et al. |
| 6,283,999 B1 | 9/2001 | Rockwood, Jr. |
| 6,306,172 B1 | 10/2001 | O'Neil |
| RE37,665 E | 4/2002 | Ralph et al. |
| 6,368,352 B1 | 4/2002 | Camino et al. |
| 6,398,812 B1 | 6/2002 | Masini |
| 6,520,994 B2 | 2/2003 | Nogarin |
| 6,524,342 B1 | 2/2003 | Muhlhausler et al. |
| 6,558,387 B2 | 5/2003 | Errico et al. |
| 6,558,425 B2 | 5/2003 | Rockwood, Jr. |
| 6,585,771 B1 | 7/2003 | Buttermilch et al. |
| 6,589,282 B2 | 7/2003 | Pearl |
| 6,620,197 B2 | 9/2003 | Maroney et al. |
| 6,626,946 B1 | 9/2003 | Walch et al. |
| 6,669,728 B2 | 12/2003 | Despres et al. |
| 6,673,114 B2 | 1/2004 | Hartdegen et al. |
| 6,679,916 B1 | 1/2004 | Frankle et al. |
| 6,719,799 B1 | 4/2004 | Kropf |
| 6,736,851 B2 | 5/2004 | Maroney et al. |
| 6,736,852 B2 | 5/2004 | Callaway et al. |
| 6,749,637 B1 | 6/2004 | Bahler |
| 6,761,740 B2 | 7/2004 | Tornier |
| 6,776,799 B2 | 8/2004 | Ball et al. |
| 6,780,190 B2 | 8/2004 | Maroney |
| 6,790,234 B1 | 9/2004 | Frankle |
| 6,863,690 B2 | 3/2005 | Ball et al. |
| 6,887,277 B2 | 5/2005 | Rauscher et al. |
| 6,899,736 B1 | 5/2005 | Rauscher et al. |
| 6,926,732 B2 | 8/2005 | Derus et al. |
| 6,942,699 B2 | 9/2005 | Stone et al. |
| 6,953,478 B2 | 10/2005 | Bouttens et al. |
| 6,969,406 B2 | 11/2005 | Tornier |
| 6,986,790 B2 | 1/2006 | Ball et al. |
| 7,011,686 B2 | 3/2006 | Ball et al. |
| 7,169,184 B2 | 1/2007 | Dall Pria |
| 2001/0011193 A1 | 8/2001 | Nogarin |
| 2001/0037152 A1 | 11/2001 | Rockwood, Jr. |
| 2001/0041940 A1 | 11/2001 | Pearl |
| 2001/0049561 A1 | 12/2001 | Dews et al. |
| 2001/0053935 A1 | 12/2001 | Hartdegen et al. |
| 2002/0016634 A1 | 2/2002 | Maroney et al. |
| 2002/0072799 A1 | 6/2002 | Despres, III et al. |
| 2002/0095215 A1 | 7/2002 | Camino et al. |
| 2002/0099445 A1 | 7/2002 | Maroney et al. |
| 2002/0120339 A1 | 8/2002 | Callaway et al. |
| 2002/0151982 A1 | 10/2002 | Masini |
| 2002/0161375 A1 | 10/2002 | Ralph et al. |
| 2003/0014119 A1 | 1/2003 | Capon et al. |
| 2003/0028253 A1 | 2/2003 | Stone et al. |
| 2003/0097183 A1 | 5/2003 | Rauscher et al. |
| 2003/0100952 A1 | 5/2003 | Rockwood, Jr. et al. |
| 2003/0114933 A1 | 6/2003 | Bouttens et al. |
| 2003/0149485 A1 | 8/2003 | Tornier |
| 2003/0158606 A1 | 8/2003 | Coon et al. |
| 2003/0204263 A1 | 10/2003 | Justin et al. |
| 2003/0229355 A1 | 12/2003 | Keller |
| 2003/0229357 A1 | 12/2003 | Dye |
| 2004/0002765 A1 | 1/2004 | Maroney et al. |
| 2004/0010262 A1 | 1/2004 | Parkinson et al. |
| 2004/0034431 A1 | 2/2004 | Maroney et al. |
| 2004/0054420 A1 | 3/2004 | Meswania |
| 2004/0064187 A1 | 4/2004 | Ball et al. |
| 2004/0064188 A1 | 4/2004 | Ball et al. |
| 2004/0064190 A1 | 4/2004 | Ball et al. |
| 2004/0073315 A1 | 4/2004 | Justin et al. |
| 2004/0094187 A1 | 5/2004 | Lee |
| 2004/0127910 A1 | 7/2004 | Pubols et al. |
| 2004/0143335 A1 | 7/2004 | Dews et al. |
| 2004/0153161 A1 | 8/2004 | Stone et al. |
| 2004/0167629 A1 | 8/2004 | Geremakis et al. |
| 2004/0181286 A1 | 9/2004 | Michelson |
| 2004/0186579 A1 | 9/2004 | Callaway et al. |
| 2004/0220673 A1 | 11/2004 | Pria |
| 2004/0220674 A1 | 11/2004 | Pria |
| 2004/0225367 A1 | 11/2004 | Glien et al. |
| 2004/0230311 A1 | 11/2004 | Cyprien et al. |
| 2004/0249467 A1 | 12/2004 | Meyers et al. |
| 2004/0267370 A1 | 12/2004 | Ondria |
| 2005/0004673 A1 | 1/2005 | Kluger |
| 2005/0033443 A1 | 2/2005 | Blatter et al. |
| 2005/0049623 A1 | 3/2005 | Moore et al. |
| 2005/0065612 A1 | 3/2005 | Winslow |
| 2005/0090824 A1 | 4/2005 | Shluzas et al. |
| 2005/0107882 A1 | 5/2005 | Stone et al. |
| 2005/0113931 A1 | 5/2005 | Horber |
| 2005/0143829 A1 | 6/2005 | Ondria et al. |
| 2005/0165490 A1 | 7/2005 | Tornier |
| 2005/0177241 A1 | 8/2005 | Angibaud et al. |
| 2005/0197708 A1 | 9/2005 | Stone et al. |
| 2005/0203631 A1 | 9/2005 | Daniels et al. |
| 2005/0203632 A1 | 9/2005 | Daniels |

(56) References Cited

U.S. PATENT DOCUMENTS

| | | |
|---|---|---|
| 2005/0251263 A1 | 11/2005 | Forrer et al. |
| 2005/0256583 A1 | 11/2005 | Bouttens et al. |
| 2005/0261775 A1 | 11/2005 | Baum et al. |
| 2005/0278030 A1 | 12/2005 | Tornier et al. |
| 2005/0278031 A1 | 12/2005 | Tornier et al. |
| 2005/0278033 A1 | 12/2005 | Tornier et al. |
| 2005/0283250 A1 | 12/2005 | Coon et al. |
| 2005/0283251 A1 | 12/2005 | Coon et al. |
| 2005/0283252 A1 | 12/2005 | Coon et al. |
| 2005/0288681 A1 | 12/2005 | Klotz et al. |
| 2005/0288791 A1 | 12/2005 | Tornier et al. |
| 2006/0009852 A1 | 1/2006 | Winslow et al. |
| 2006/0020344 A1 | 1/2006 | Shultz et al. |
| 2006/0036328 A1 | 2/2006 | Parrott et al. |
| 2006/0069445 A1 | 3/2006 | Ondria et al. |
| 2006/0116768 A1 | 6/2006 | Krueger et al. |
| 2007/0162145 A1 | 7/2007 | Justin et al. |
| 2007/0173945 A1 | 7/2007 | Wiley |
| 2008/0147203 A1 | 6/2008 | Cronin |
| 2008/0228281 A1 | 9/2008 | Forrer et al. |
| 2009/0187251 A1 | 7/2009 | Justin et al. |

FOREIGN PATENT DOCUMENTS

| | | |
|---|---|---|
| DE | 3914809 A1 | 11/1990 |
| DE | 4128259 A1 | 3/1993 |
| DE | 19606057 C2 | 8/1997 |
| DE | 29918669 U1 | 12/1999 |
| DE | 29918669 U1 | 3/2000 |
| EP | 0190093 A1 | 8/1986 |
| EP | 0337513 B1 | 10/1989 |
| EP | 0350435 A1 | 1/1990 |
| EP | 0530585 B1 | 3/1993 |
| EP | 0621018 A1 | 10/1994 |
| EP | 0631497 B1 | 1/1995 |
| EP | 06793785 A1 | 11/1995 |
| EP | 0552950 B1 | 9/1996 |
| EP | 0853928 A1 | 7/1998 |
| EP | 0927548 A2 | 7/1999 |
| EP | 1004283 A2 | 5/2000 |
| EP | 1059070 B1 | 12/2000 |
| EP | 1093777 A2 | 4/2001 |
| EP | 1125565 A2 | 8/2001 |
| EP | 1216668 A2 | 6/2002 |
| EP | 1314407 A1 | 5/2003 |
| EP | 0828459 B1 | 9/2003 |
| EP | 1415621 A2 | 5/2004 |
| EP | 0956836 B1 | 7/2004 |
| EP | 1449500 A2 | 8/2004 |
| EP | 1472999 A1 | 11/2004 |
| EP | 1527757 A1 | 5/2005 |
| EP | 1543801 A1 | 6/2005 |
| EP | 1364623 B1 | 10/2005 |
| EP | 1591084 A1 | 11/2005 |
| EP | 1598034 A1 | 11/2005 |
| EP | 1393697 B1 | 2/2006 |
| EP | 1951161 A1 | 8/2008 |
| FR | 2617040 A1 | 12/1988 |
| FR | 2627983 A1 | 9/1989 |
| FR | 2652498 A1 | 4/1991 |
| FR | 2674122 A1 | 9/1992 |
| FR | 2699400 A1 | 6/1994 |
| FR | 2704747 A1 | 11/1994 |
| FR | 2748389 A1 | 11/1997 |
| FR | 2776506 A1 * | 10/1999 |
| FR | 2799115 A1 | 4/2001 |
| FR | 2825263 A1 | 12/2002 |
| GB | 2069338 A | 8/1981 |
| GB | 2268408 A | 1/1994 |
| GB | 2405346 A | 3/2005 |
| JP | 11503351 T | 3/1999 |
| JP | 2004113804 A | 4/2004 |
| JP | 2004121850 A | 4/2004 |
| WO | WO96/32071 A1 | 10/1996 |
| WO | WO98/08467 A1 | 3/1998 |
| WO | WO00/72784 A1 | 12/2000 |
| WO | WO02/07647 A3 | 1/2002 |
| WO | WO2005/032430 A1 | 4/2005 |
| WO | WO-2007057054 A1 | 5/2007 |
| WO | WO2007/082925 A1 | 7/2007 |

OTHER PUBLICATIONS

Katz et al. Machine Translation of FR 2776506A1 Date: Oct. 1999.*
Surgical Technique, Delta CTA Reverse Shoulder System—DuPuy (delta) 2004.
Article—Initial Glenoid Component Fixation in "Reverse" Total Shoulder Arthroplasty: A Biomechanical Evaluation, Harman et al., In press JSES 2005 (harman).
Webpage and Patient Information—Baylor College of Medicine, Reverse Total Shoulder Arthroplasty, Jeffrey E. Budoff, M.D., Department of Orthopaedic Surgery, last modified Mar. 30, 2006: http://www.bcm.edu/ortho/md/budoff/patienteducation/reversetotalshoulderarthroplasty.htm (budoff).
ProNews, a Publication of Zimmer Group, Swiss Edition Mar. 2004, 12 pages, of interest, p. 8 (pronews).
Article from Medscape Today, WebMD, Shoulder Arthroplasty, Andrew H. Schmidt, M.D. accessed Dec. 3, 2004 (schmidt).
Article—The Reverse Shoulder Prosthesis for Glenohumeral Arthritis Associated with Severe Rotator Cuff Deficiency, Mark Frankle, MD et al., 2005 by the Journal of Bone and Joint Surgery, Incorporated, pp. 1697-1705 (Frankle).
Office Action mailed Mar. 15, 2010 in U.S. Appl. No. 12/412,129.
Amendment filed May 5, 2010 in U.S. Appl. No. 12/412,129.
Final Office Action mailed Jul. 21, 2010 in U.S. Appl. No. 12/412,129.
Amendment filed Sep. 28, 2010 in U.S. Appl. No. 12/412,129.
The Office Action mailed Feb. 28, 2007 in European application No. 04256209.0.
The Office Action mailed Jul. 10, 2009 in Australian application No. 2004218735.
The Response filed Oct. 22, 2009 to the Office Action mailed Jul. 10, 2009 in Australian application No. 2004218735.
The Office Action mailed Oct. 29, 2009 in Australian application No. 2004218735.
The Partial European Search Report issued Aug. 5, 2009 in European Application No. EP08017942.7.
"Australian Application Serial No. 2006314835, Office Action mailed Mar. 20, 2012", 2 pgs.
"International Application Serial No. PCT/EP2006/000370, International Preliminary Report on Patentability mailed Mar. 3, 2008", 7 pgs.
"International Application Serial No. PCT/EP2006/000370, International Search Report mailed Jul. 11, 2006", 4 pgs.
"International Application Serial No. PCT/EP2006/000370, Written Opinion mailed Jul. 11, 2006", 8 pgs.
Surgical Technique—Anatomical Shoulder System, 36 pages, 06-006-070-12 Rev. 1 5ML, 2004 Zimmer, Inc. (Anatomical_Shoulder_System_Surgical_Technique_06-006-070-12_Rev.pdf).
Website—www.tornier-us.com/product_shldr_aqu.htm#—last accessed Feb. 27, 2006 (tornier).

* cited by examiner

Fig. 1

(PRIOR ART)

BASE PLATFORM FOR AN ARTIFICIAL JOINT

CROSS-REFERENCE TO RELATED APPLICATIONS

This application is a U.S. National Phase Patent Application based on International Application Serial No. PCT/EP2006/000370 filed Jan. 17, 2006, the disclosure of which is hereby explicitly incorporated by reference herein.

BACKGROUND

The invention relates to a base platform for an artificial joint. The invention further relates to an artificial joint component made either as a shell or socket or as a ball or head. The invention furthermore relates to a joint part comprising a base platform of this type and a joint component of this type. The invention further relates to a modular kit for the forming of different joint parts comprising at least one platform of this type and a plurality of different joint components of this type. The invention moreover relates to a method of implanting an artificial joint comprising a joint part in accordance with the invention having a platform in accordance with the invention.

The invention can generally be used for all joints and is described in the following for the example of a shoulder joint which represents a possible field of application for the invention.

With shoulder joints, but also with other joints, there is a problem in that the selection of the suitable implant and the manner of implanting decisively depend on the state in which the bones involved are, with the state of the muscles, in particular of the rotator cuff, playing a role. With the shoulder joint, the state of the shoulder blade (scapula) is particularly important, and above all in this context the state of the joint socket (glenoid) which cooperates with the head of the upper arm (humerus) in the healthy joint. The necessity of a part replacement or complete replacement of the shoulder joint can be present for various reasons. Typical causes are, for example, advanced wear of the joint surfaces or fractures, e.g. due to an accident.

Depending on the type and degree of damage, a so-called inverse prosthesis configuration can also be indicated in which the artificial joint ball and the artificial joint shell are swapped over with respect to their positions in a natural joint.

It is a problem that the surgeon can frequently only make the correct decision on the type of the prosthesis and its attachment during the operation. Furthermore, an initially made selection can admittedly prove correct for a first treatment, but may later turn out to require a change, which has the consequence of another operation and the risks for and strain on the patient associated with it.

There is therefore a need for possibilities to carry out the implanting of joint prostheses in as simple and as flexible a manner as possible and with the lowest possible risks and strains for the patient. This is where the invention comes in.

SUMMARY

An aspect of the invention relates to a base platform having the features of claim 1.

The platform in accordance with the invention can serve both for an artificial shell or socket (anatomic configuration) and for a ball or a head (inverse configuration) and is thus anchored to the bone, which in particular forms the natural joint socket; that is in the case of a shoulder joint to the shoulder blade, i.e. in particular to its glenoid.

In accordance with the invention, different joint components can be mounted to the platform. In this context, "can be mounted" is to be understood such that, with the platform anchored to the bone—that is during an operation—a joint component can be attached to the platform, with it also being possible, with the platform anchored to the bone, to exchange a joint component mounted on the platform for another joint component. In accordance with the invention, an artificial shell component can be exchanged for an artificial ball component, and vice versa, while maintaining the base platform, since the platform is designed both for an anatomical configuration and for an inverse configuration.

A further aspect of the invention relates to a joint component for an artificial joint, in particular for an artificial shoulder joint having the features of claim 17.

A further aspect of the invention relates to a joint part for an artificial joint, with the joint part comprising a platform in accordance with the invention and a joint component in accordance with the invention anchored to the platform. The joint part in accordance with the invention can thus be realized both in an anatomical configuration and in an inverse configuration.

In accordance with a further aspect, the invention relates to a modular kit for the forming of different joint parts, with the modular kit comprising at least one platform in accordance with the invention as well as a plurality of different artificial joint components which are made in each case as shell components or as ball components. This modular kit allows the surgeon to form the respectively best fitting joint part during the operation. This applies both to a first treatment and to any revision which may become necessary.

A further aspect of the invention relates to a method of implanting an artificial joint, wherein a joint part in accordance with the invention is present in a starting configuration and this starting configuration is changed into an end configuration in that an artificial joint component anchored to the platform of this joint part in accordance with the invention is exchanged for another artificial joint component.

It is in particular possible in this process for an anatomical configuration to be changed into an inverse configuration, and vice versa. If the change of configuration should take place within the framework of a revision, it is of advantage in accordance with the invention for the platform to be able to remain anchored to the bone.

Further embodiments of the invention are also recited in the dependent claims, in the description and in the drawing.

The platform can have a pin by which a fastening of the platform to the bone can take place (primary anchorage) and which is simply hammered into a correspondingly prepared recess in the bone. The pin can taper, in particular conically. The primary anchorage can optionally be supported by additional anchoring screws (secondary anchorage). These anchoring screws can be polyaxial screws for which the platform in accordance with the invention can be provided with corresponding screw mounts in addition to a pin. Polyaxial screw anchoring connections of this type are generally known in connection with bone plates for osteosynthesis. The base platform in accordance with the invention can be anchored to the bone by means of the polyaxial anchoring screws in an orientation of the anchoring screws optimized with regard to the respective circumstances.

A high degree of flexibility in joint operations is hereby provided since the platform can serve as a base both in an anatomical configuration and in an inverse configuration and since a secure and reliable anchorage to the bone is possible even in difficult situations due to the possibility of providing screw mounts for polyaxial anchoring screws in addition to a (conical) pin.

The pin can have an outer cross-sectional shape differing from a circular shape over at least part of its length. The cross-sectional shape can be oval or elliptical, for example.

A central axis of the pin and central axes of at least two screw mounts can be disposed in a common main plane. The platform can have a basic shape which differs from a circular shape and which has a plane of symmetry which coincides with the common main plane.

If the pin has an oval or an elliptical outer cross-sectional shape over at least a part of its length whose one main axis, in particular its long main axis, lies in a common plane and if the platform has a basic shape which differs from a circular shape and has a plane of symmetry which coincides with the common main plane, a base platform results overall with a well-defined and clearly identifiable preferred direction. This not only allows the surgeon to align the platform in a defined manner relative to the bone, but above all also to align the artificial joint component to be attached to the platform in a defined manner relative to the platform. This is in particular of advantage when the joint component is provided with an asymmetric or eccentric design which makes it necessary for the surgeon to fix the joint component in a specific position relative to the bone.

At least two screw mounts of the platform can be made such that their central axes face in different directions. A spreading or clamping of the platform at the bone by means of polyaxial anchoring screws held by the screw mounts is hereby facilitated.

If the screw mounts each have an anchoring collar which projects from the platform on the same side as the pin, the primary anchorage established with the conical pin can hereby be supported. If the central axes of the screw mounts and thus the anchoring collar face in different directions, a spreading or clamping can already be achieved by the anchoring collars even if no polyaxial anchoring screws are used.

The screw mounts can have means with which the polyaxial anchoring screws can be fixed within predetermined limits in any desired orientation relative to the platform. The means can each comprise a thread section for a fixing nut which cooperates with a head of the polyaxial anchoring screw.

The platform can be made of metal.

The platform can be made in one piece.

The platform can have at least one release cut-out in the end region of its side facing the joint component when the artificial joint component is anchored, said release cut-out being accessible from the outside and being in particular of pocket-shape and with a release instrument being able to be introduced or applied to said release cut-out for the release of the anchorage of the joint component to the platform. Analogously, a release cut-out of this type can—alternatively or additionally—also be formed at the artificial joint component.

The pin of the base platform in accordance with the invention can be hollow and be made for the reception of a fixing section of the artificial joint component. The joint component can then be anchored to the platform via its fixing section. The fixing section of the joint component can have an outer side which tapers, in particular conically.

The inner cross-sectional shape of the pin can correspond to the outer cross-sectional shape of the pin.

If the pin of the platform is hollow and serves for the mounting of a fixing section of the artificial joint component to anchor the artificial joint component to the platform via its fixing section, the pin can have an inner cross-sectional shape differing from a circular shape over at least a part of its length. This inner cross-sectional shape can be oval or elliptical.

The connection between the pin of the platform and the fixing section of the artificial joint component can be a clamp connection or a press-fit connection, in particular a conical press-fit, with a latch connection or snap-in connection alternatively being able to be provided. Generally, the connection between the pin and the fixing section can be made either as force-transmitting or shape matched. The connection can generally be self-locking.

The advantage of a force-transmitting connection, in particular of a press-fit, between the pin and the fixing section consists of a particularly firm and stable connection being able to be achieved in a simple manner, wherein in particular the risk of particle abrasion and/or of premature loosening is reduced. With a corresponding geometric design of the pin and of the fixing section, the connection between the platform and the joint component can be established in a particularly simple manner in that, for example, the fixing section of the joint component can be hammered into the pin of the platform by a single blow with a defined blow force onto the joint component. In the case of a connection with tapering parts, in particular of a conical connection, a uniform tensioning along the total effective inner side of the pin can hereby be achieved.

The pin and the fixing section can be made such that the inner side of the pin and the outer side of the fixing section contact one another either over their total periphery or only at a plurality of linear or strip-shaped regions distributed discretely over the periphery. This contact does not have to be over the whole length of the pin or of the fixing section, with this, however, also not being precluded.

The artificial joint component can have a shell section or a ball section and a fixing section. The fixing section can be arranged either centrally or eccentrically with respect to the shell section or ball section. The type of the arrangement can be dependent on the dimensions of the shell section or of the ball section, e.g. on the diameter of the ball. With an eccentric arrangement, what is important on the insertion of the artificial joint component is its orientation relative to the bone and thus—when the joint component cannot be anchored to the platform in any desired orientation relative to it—the orientation of the platform relative to the bone.

The artificial joint component can be made in multiple parts.

The joint component can comprise a separate fixing piece which forms a fixing section for anchorage to the platform and is fixedly connected to a shell section or a ball section of the joint component. It is in particular possible due to this multi-part design of the artificial joint component to manufacture the shell section or ball section, on the one hand, and the fixing piece, on the other hand, from different materials. The shell section or the ball section can thus be matched directly to its respective mating piece with which it forms the actual joint connection, whereas the fixing piece can be optimized with respect to the anchorage of the shell section or ball section to the platform.

The separate fixing piece can in particular be made with respect to an optimum material pairing with the pin of the platform. The shell section or ball section can be made of plastic and the separate fixing piece of metal. If the platform in accordance with the invention is made of metal, a metal-to-metal connection can be realized in this way between the separate fixing piece of the joint component, on the one hand, and the pin of the platform, on the other hand. A material pairing of this type is of advantage for the establishing of a force-transmitting connection, in particular a press-fit connection.

The separate fixing piece can be resilient with respect to forces which become effective on the establishment of a force-transmitting connection to the pins of the platform. A resilience of this type can be realized in that the separate fixing piece is provided with one or more longitudinal slots.

The fixing piece can have a flange-like foot section via which the fixing piece is connected to the shell section or ball section of the joint component.

The connection between the fixing piece and the shell section or ball section of the joint component can take place without additional fastening means. The shell section or ball section can be made of plastic and can be connected to the fixing piece, in particular to its flange-like foot section, by pressing. For this purpose, the foot section can be provided with one or more bores with which the plastic material of the joint component can enter into an intimate force-transmitting connection by the pressing. The plastic material of the joint component can be softened by warming for the pressing.

The shell section or ball section can also be made of metal.

The platform and the joint component can be made such that the anchorage can be released without damage to the platform.

For this purpose, the joint component can be provided with at least one thread section for a screw-in press-off instrument. The thread section can be provided in the form of an internal thread of the fixing section and/or of a threaded bore in a flange-like foot section of a separate fixing piece.

Alternatively or additionally, the joint component and the platform can together bound at least one release cut-out which is accessible from the outside and into which or at which a release instrument for the release of the connection between the joint component and the platform can be introduced or fixed. The cut-out can be formed either at the joint component or at the platform, with it also being possible for part cut-outs formed at the joint component and at the platform to form a release cut-out together in the assembled state.

The artificial joint component can be provided with anchorage projections which engage into the screw mounts of the platform. A joint component of this type can be used when a primary anchorage of the platform to the bone via its pin is sufficient and the screw mounts are not needed for anchoring screws.

BRIEF DESCRIPTION OF THE DRAWINGS

The invention will be described in the following by way of example with reference to the drawing. There are shown.

DETAILED DESCRIPTION

As already initially mentioned, the invention can generally be used in conjunction with any desired joints. A possible area of use is the shoulder joint. Before different embodiments of the invention are presented in detail with reference to FIGS. 3 to 8, an introductory overview should first be given with reference to FIGS. 1 and 2, and indeed for the example of the shoulder.

Figure 1:
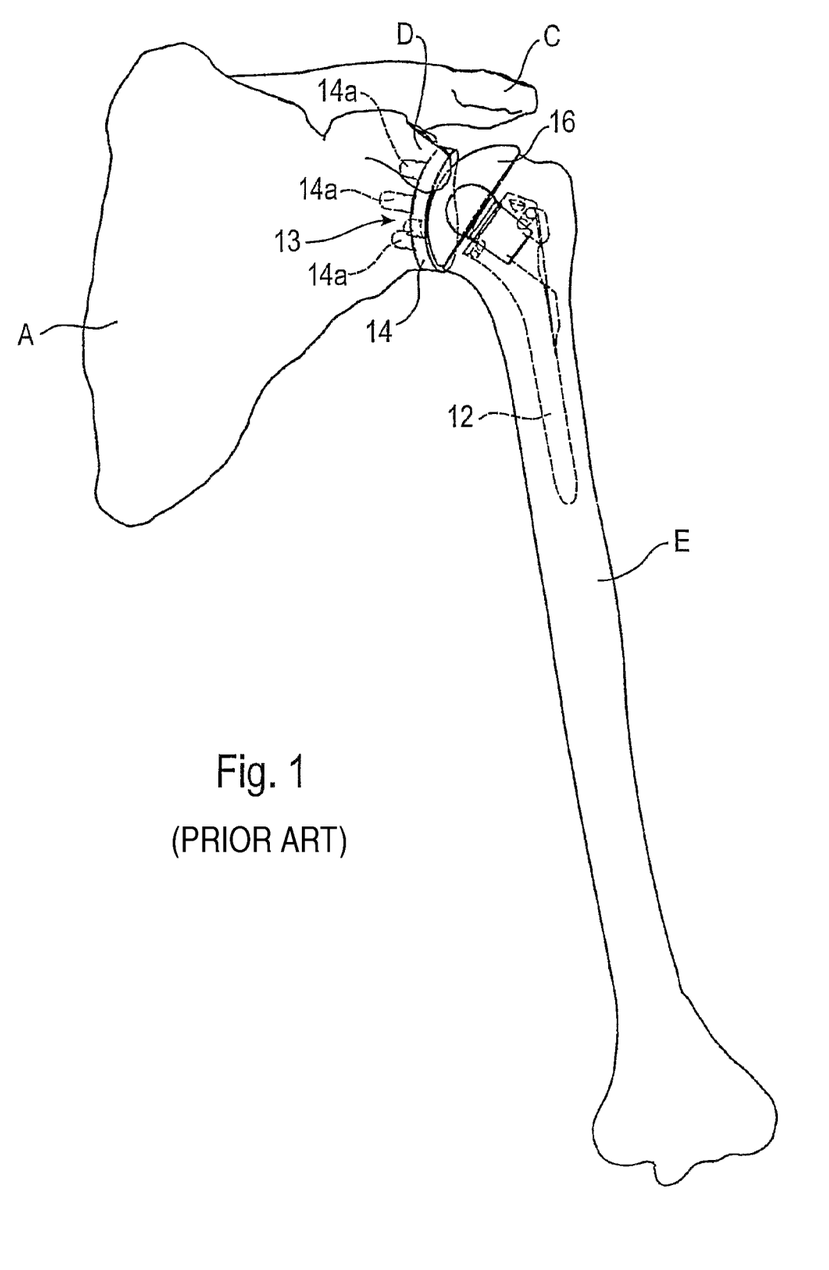
FIGS. 1 and 2 an artificial shoulder joint in an anatomical configuration (FIG. 1) and inverse configuration (FIG. 2)
Figure 2:
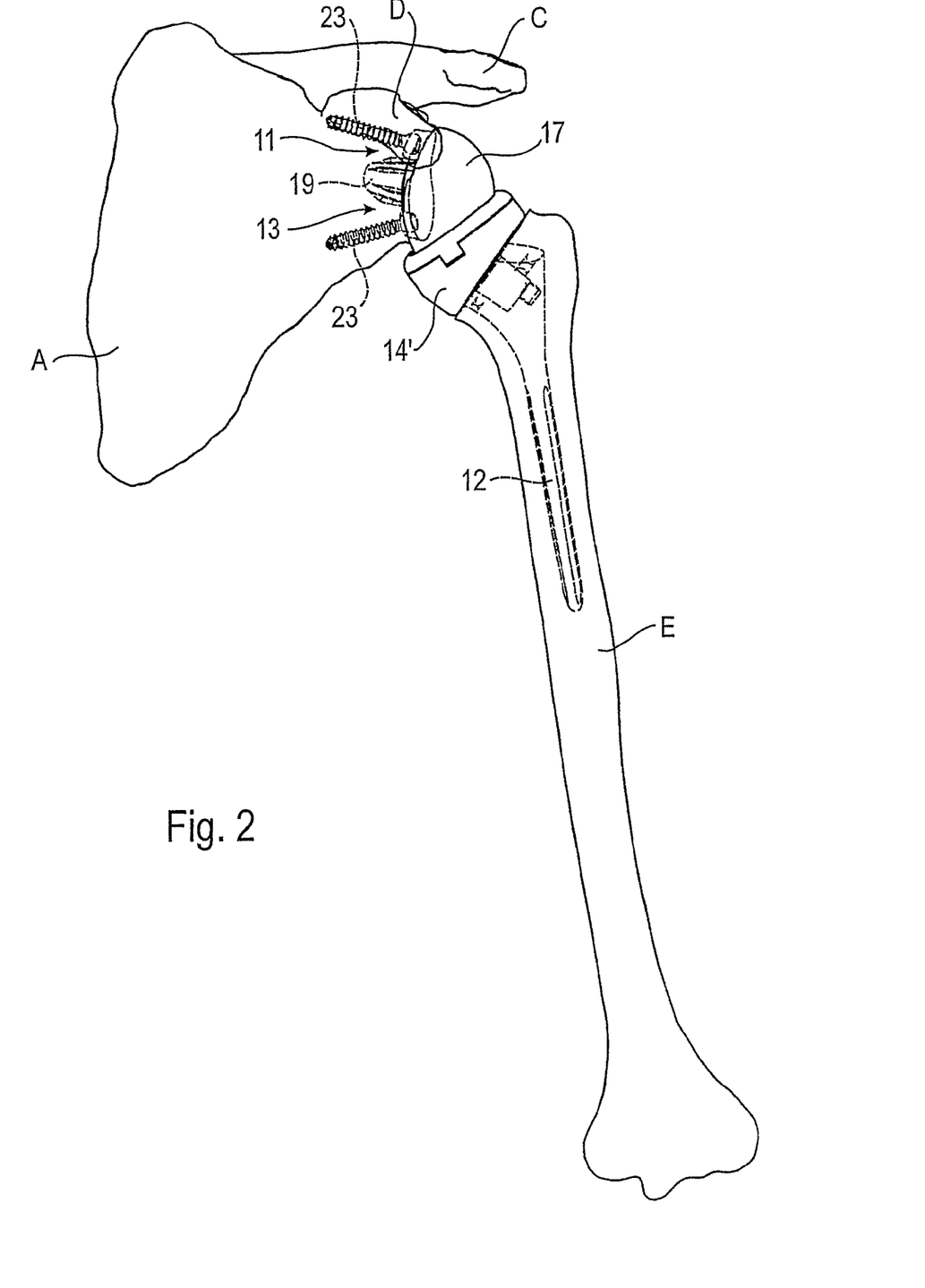

The bony structure of the shoulder joint, and only this should be looked at here, consists of the head of the upper arm bone (humerus) E and of the joint socket (glenoid) B of the shoulder blade A. In addition, two bone projections of the shoulder blade A, namely the acromion C and the coracoid D are important for the function of the shoulder blade. These bone projections, together with a ligament (not shown) connecting them, form the so-called "ceiling" of the shoulder which has an arch-like shape and prevents an upward migration of the head of the upper arm from the joint socket.

FIG. 1 shows a so-called anatomical configuration in which the prosthesis reproduces the shoulder joint in its natural structure, i.e. the humerus E is provided with an artificial joint head 16 and the shoulder blade A is provided with an artificial joint socket 14. The joint socket 14 is here not formed by an artificial joint part in accordance with the invention, but this is possible, as was already initially explained. FIG. 1 is only intended to give an overview here.

The anchorage of the joint socket 14 at the shoulder blade A, more precisely at the correspondingly prepared glenoid B, takes place via screws 14a in the example shown. The anchorage of the artificial joint head 16 to the humerus E takes place by means of a shaft 12 which can have different types of design. The specific aspect of the part of the artificial shoulder joint at the humerus side is not a subject of the invention so that it will not be looked at in more detail in the following.

FIG. 2 shows a so-called inverse configuration in which the artificial joint head and the artificial joint socket 14' have been swapped over with respect to their positions in the natural shoulder joint. The joint head is here formed by an artificial joint part in accordance with the invention which comprises a base platform 11 in accordance with the invention and a ball component 17 firmly connected to the platform 11. The anchorage of the platform 11 to the shoulder blade A, more precisely to the correspondingly prepared glenoid B, takes place in the example shown via a conical pin 19 of the platform 11 provided with ribs and by means of polyaxial anchoring screws 23 for which corresponding screw mounts are provided in the platform 11. The pin 19 forms a primary anchorage for the platform 11, whereas the anchoring screws 23 forming an—optional—secondary anchorage can also be omitted in dependence on the respective circumstances.

Whereas therefore the platform 11 here supports the artificial ball component 17, an artificial joint socket 14' is anchored to the humerus E by means of a shaft 12.

Special features of the invention are inter alia the design of the platform 11 and the manner of its attachment to the glenoid B. Details on this and on the specific structure of the platform 11 and on the respective artificial joint component 15 (shell) or 17 (ball) can be seen from the following description.

The base platform 11 in accordance with the invention can be identical for all variants described in the following. The platform 11 is in each case made in one piece and completely of metal. The respective joint component 15, 17 (FIGS. 3, 4 and 5) or a shell section 35 (FIGS. 6, 7 and 8) or ball section (not shown), which forms the joint component 15, 17 together with a metallic insert 33, can generally each be manufactured either of plastic, for example of polyethylene, or of metal. In particular the ball component 17 or the ball section are made of metal.

Figure 3:
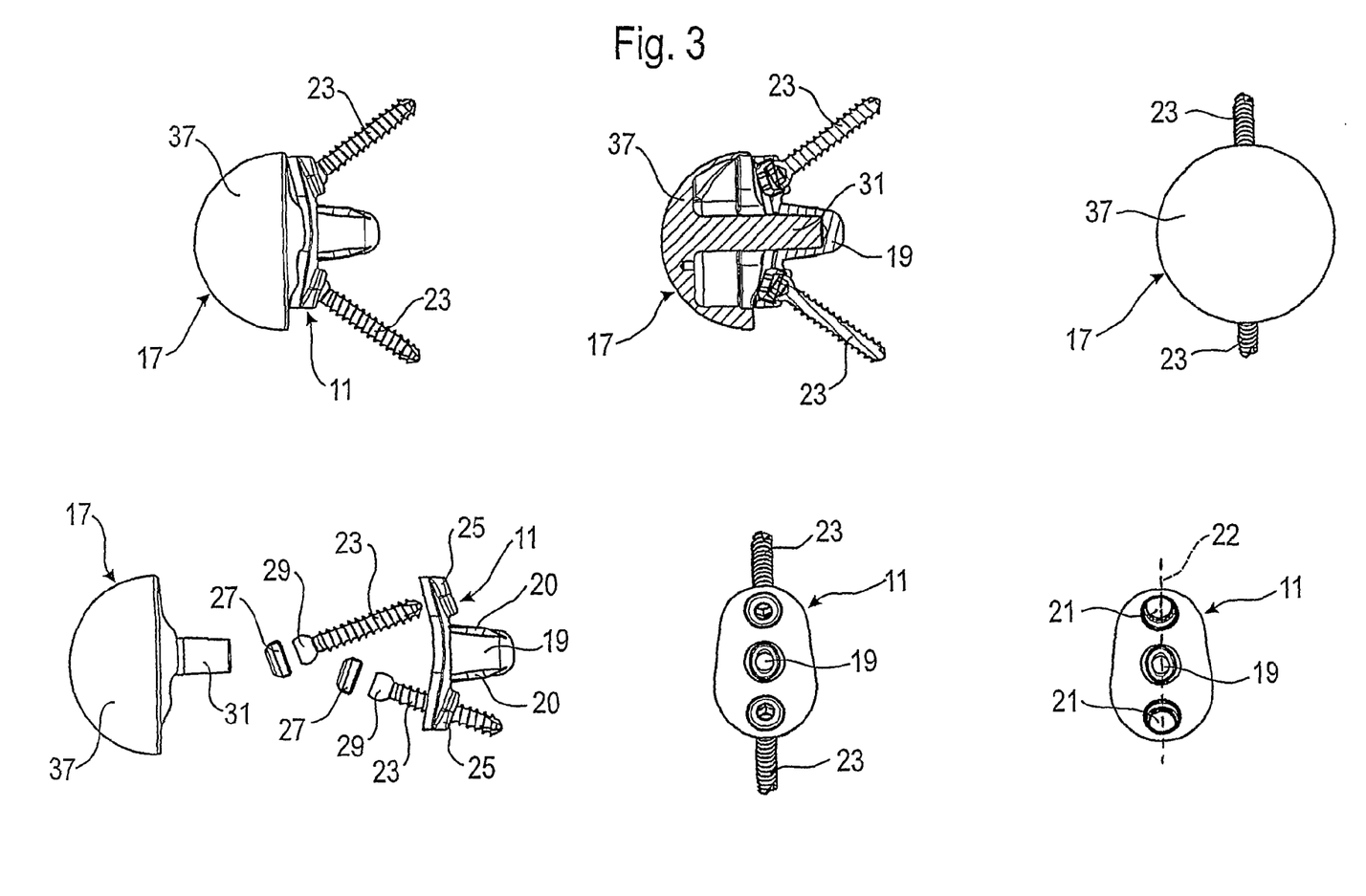
FIG. 3 different views of a joint part in accordance with the invention for an inverse configuration in accordance with an embodiment of the invention.

FIG. 3 shows an artificial joint part for an inverse configuration. A platform 11 is connected to a ball component 17. The platform 11 comprises a shell-like base part with a convex side and a concave side. A pin 19 projects from the convex side and tapers and, in this embodiment, has a conical outer side which is provided with longitudinal ribs 20.

Furthermore, two collars 25 project from the convex side and their central axes each coincide with a central axis of a passage 21 formed in the platform 11. The passages 21 are made as screw mounts 21 for polyaxial anchoring screws 23. The anchoring screws 23 are introduced from the concave side of the platform and are fixed by fixing nuts 27 which are provided with an external thread in the screw mounts 21 in a respectively desired orientation relative to the platform 11. For this purpose, the screw mounts 21 are each provided with a corresponding internal thread. The fixing nuts 27 clamp the heads 29 of the anchoring screws 23 tightly in the screw mounts 21.

The central axes of the screw mounts 21, and thus the anchoring collars 25, face in different directions, with these directions running apart in V shape starting from the convex side of the platform 11, and indeed symmetrically to the central axis of the pin 19. As the representation at the bottom right in FIG. 3 shows, the central axes of the screw mounts 21 and the central axis of the pin 19 are disposed in a common plane 22 which is also called a main plane in the following.

The platform 11 has an oval base shape with a width reducing along its longitudinal axis, with a plane of symmetry containing the longitudinal axis coinciding with the aforementioned main plane 22.

The conical pin 19 has an elliptical outer cross-sectional shape whose longer main axis is disposed in the main plane 22.

The ball component 17 is provided with a fixing section 31 which is made as a conical pin. The fixing pin 31 of the ball component 17 likewise has an elliptical outer cross-sectional shape. The pin 19 of the platform 11 is hollow to receive the fixing pin 31 and has an internal cross-sectional shape formed elliptically in accordance with the fixing pin 31.

The fixing pin 31 of the ball component 17 is hammered into the conical mount formed by the pin 19 of the platform 11 to fix the ball component 17 to the platform 11, whereby a press-fit connection is established which is in particular a conical press fit.

The fixing pin 31 of the ball component 17 is arranged eccentrically with respect to a ball section 37. The deviation from the circular shape in the fixing pin 31 of the ball component 17 and in the pin 19 of the platform 11 permits a direct alignment of the ball component 17 relative to the platform 11. A central arrangement of the fixing pin 31 is generally also possible.

Figure 4:
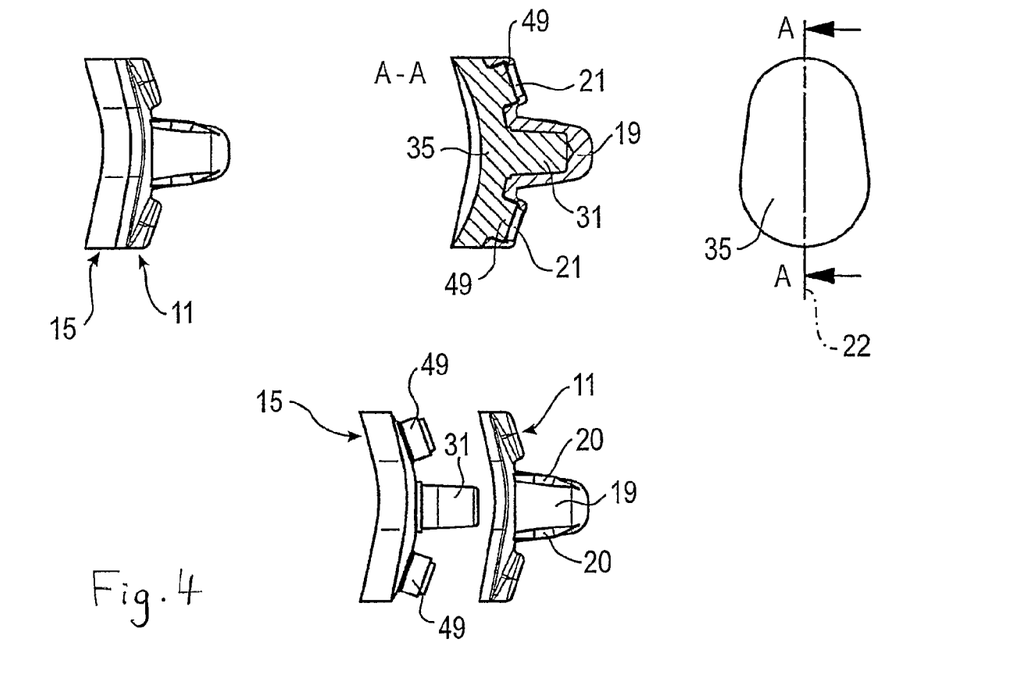
FIGS. 4 to 8 respective different views of a further embodiment of a joint part in accordance with the invention for an anatomical configuration.
Figure 5:
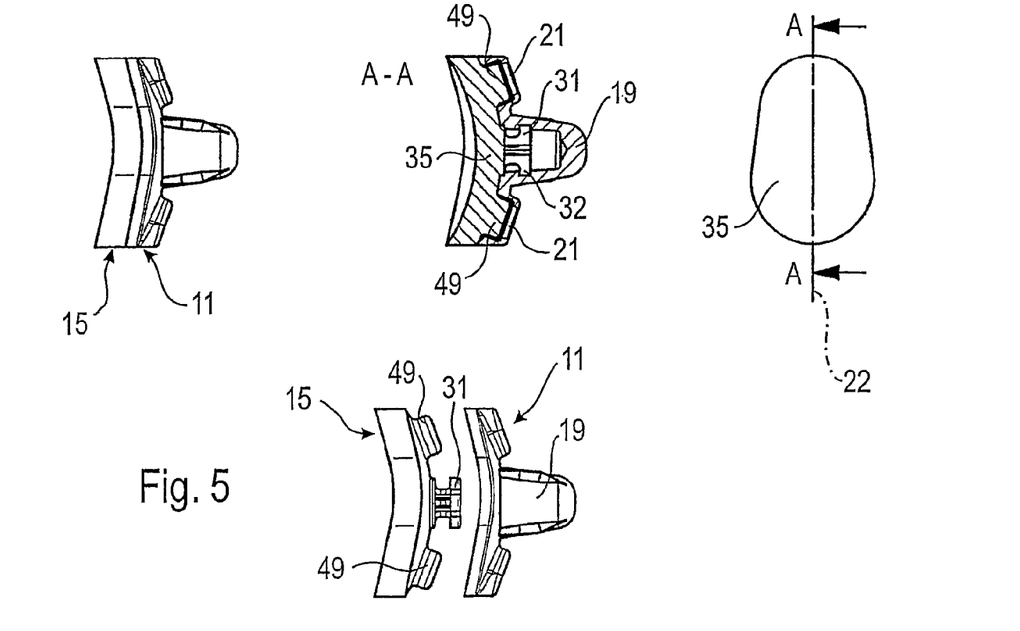

FIGS. 4 and 5 show embodiments for an anatomical configuration. The artificial joint component is made as a shell component 15 which is fixed to the platform 11 via a fixing section 31.

The two variants shown in FIGS. 4 and 5 differ by the design of their fixing section 31 which is made integrally with the shell section 35 in both variants.

In the embodiment of FIG. 4, the fixing section 31 is made in accordance with the embodiment of FIG. 3 as a conical pin which is hammered into a corresponding conical mount of the pin 19 of the platform 11 to establish a pure force-transmitting connection in the form of a press fit.

In the variant in accordance with FIG. 5, the fixing section 31 is shortened with respect to the embodiment of FIG. 4 and is provided at its free end with a ring projection 32 which engages in the assembled state into a ring groove which is formed at the inner side of the hollow pin 19 of the platform 11. To achieve a resilient deformability, the fixing section 31 can be divided into a plurality of deflectable segments e.g. by the formation of slots. The fixing section 31 of the shell component 15 is plugged so far into the hollow pin 19 of the platform 11 until the ring projection 32 latches into the ring groove.

In the embodiments of FIGS. 4 and 5, the inner cross-sectional shape of the pin 19 and the outer cross-sectional shape of the fixing section 31 can also differ from a circular shape in the region of the ring projection 32 and can be elliptical for example.

The ring groove in the pin 19 can be formed in a conical inner side which is suitable for the reception of a conical pin 31 in accordance with the embodiments of FIGS. 3 and 4, whereby the platform 11 can be used universally. It has been found that a ring groove of this type does not impair the establishment of a press fit connection with a conical pin. A platform 11 provided with a ring groove in the pin 19 can therefore be used both for a force transmitting press fit connection in accordance with FIGS. 3 and 4 and for a shape matching latch connection or snap-in connection in accordance with FIG. 5.

In both variants of FIGS. 4 and 5, the artificial shell component 15 is additionally provided with two anchorage projections 49 which engage into the screw mounts 21 of the platform 11 in the assembled state. A particularly secure connection between the artificial joint component 15 and the platform 11 is hereby achieved which can be established by pressing on the manufacture of the joint part.

The joint parts in accordance with FIGS. 4 and 5 are each an ex works starting configuration for the primary treatment of a patient. The joint part is implanted in the assembled state so that an anchorage of the platform 11 to the glenoid takes place only by the pin 19. An only primary anchorage of this type is completely sufficient in many cases.

A configuration in accordance with FIGS. 4 and 5 is generally also possible with an artificial ball component instead of the shell component 15 shown.

The joint component 15 consisting of plastic can be released from the platform 11, and indeed without damaging the platform 11. The release of the joint component 15 can take place with the platform 11 already anchored to the glenoid. The joint component 15 is destroyed by cutting up and/or by drilling open in this process.

The shell component 15 can subsequently be replaced by another shell component, e.g. in accordance with the embodiments of FIGS. 6-8, with an additional secondary anchorage of the platform 11 to the glenoid optionally being able to be carried out beforehand by polyaxial anchoring screws which can be introduced via the now accessible screw mounts 21. It is also possible to replace the shell component 15 with a ball component, e.g. in accordance with FIG. 3, if it should be found that the shoulder of the patient is not suitable for an anatomical prosthesis configuration such as is given in the variants of FIGS. 4 and 5.

Figure 6A:
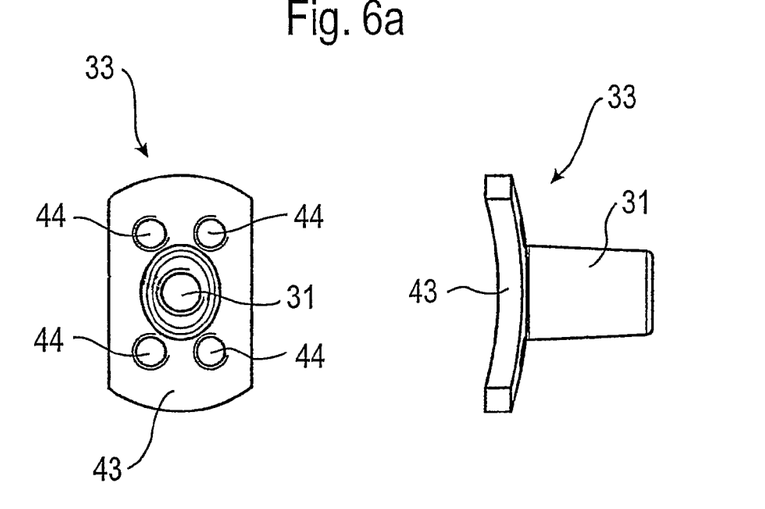
Figure 6B:
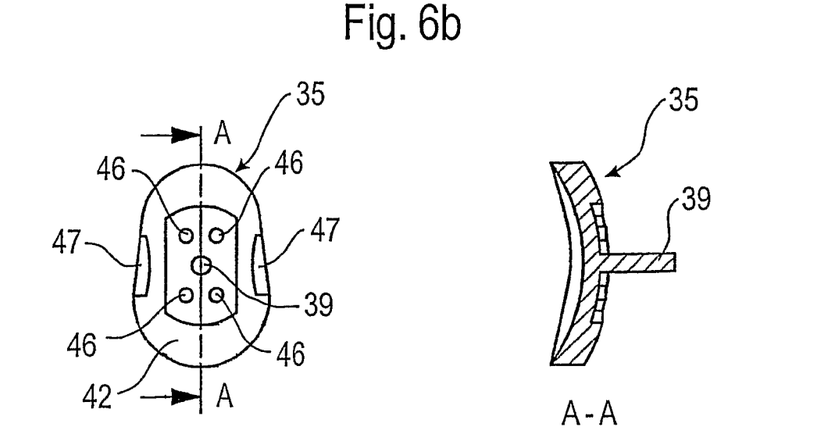
Figure 6C:
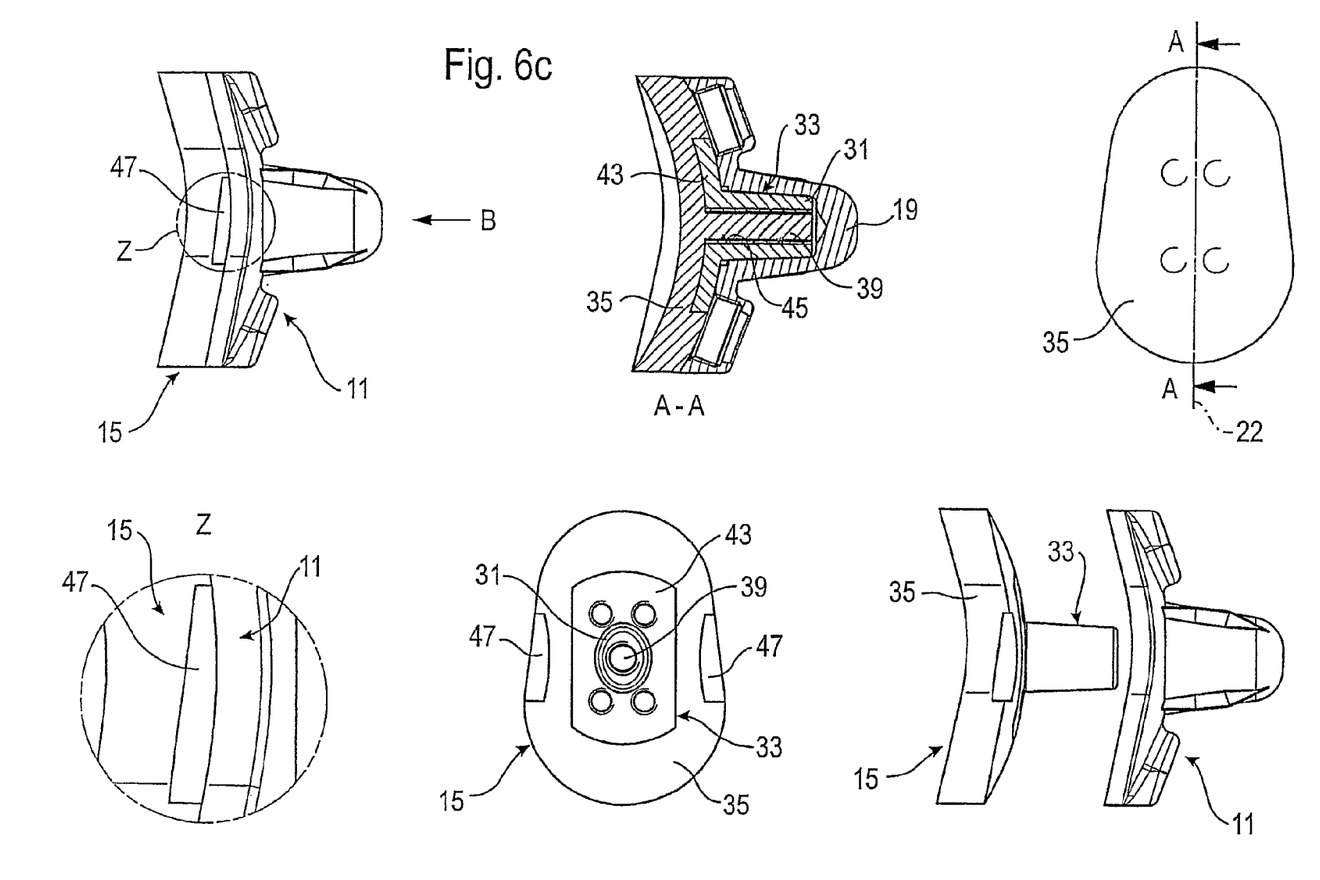

In the embodiment of FIGS. 6a-6c, the artificial joint component 15 shown as a shell here is made in multiple parts. The shell component 15 comprises a shell section 35 (FIG. 6b) manufactured of plastic and a separate fixing piece 33 (FIG. 6a) made of metal and also called an insert in the following.

The fixing piece 33 has a plate-shaped, curved foot section 43 which is provided with a plurality of bores 44. The bores 44 can be provided with an internal thread. The foot section 43 and in particular the bores 44 serve for the fastening of the insert 33 to the shell section 35. This fastening takes place by pressing, with the plastic material of the shell section 35 being previously softened by warming. The bores 44 in the foot section 43 of the insert 33 and—if present—their internal threads provide an intimate shape matching connection between the insert 33 and the shell section 35.

Furthermore, the foot section 43 is provided with a conical pin which forms a fixing section 31 of the insert 33. The shell component 15 can be anchored to the platform 11 as a whole by the fixing section 31 (FIG. 6c). In this embodiment, the fixing section 31 of the insert 33 is made as a complete cone. With an established press fit connection, the conical fixing section 31 consequently contacts the correspondingly conical inner side of the hollow pin 19 of the platform 11 in a fully areal manner.

As the section A-A in FIG. 6c shows, the insert 33 is provided with a throughgoing internal thread 45. To release the shell component 15 from the platform 11, after the destructive removal of the shell section 35, a press-off instrument made, for example, as a press-off screw can be screwed into the insert 33 still firmly seated in the pin 19 of the platform 11 until the press-off instrument is supported at the base of the pin 19 and then presses the insert 33 out of the pin 19 on a further screw movement.

The internal thread 45 of the insert 33 can—in deviation from the embodiment of FIGS. 6a-6c-end before the free end of the fixing section 31.

The threaded bores 44 of the foot section 43 can also be used for the pressing off by means of a screw-in press-off instrument.

A spike-like continuation 39 of the shell section 35 serves as a carrier for the insert 33 and substantially completely fills up the interior of the fixing section 31.

Furthermore, the shell section 35 is provided with two pocket-like release cut-outs 47. The cut-outs 47 are each open outwardly at the side and in the direction of the platform 11 and serve for the release of the shell section 35 from the insert 33. For this purpose, correspondingly shaped instruments can be introduced into the cut-outs 47 to apply lever forces onto the shell section 35 while being supported at the platform 11.

The position and the shape of the release cut-outs 47 can in particular be recognized in the left hand central representation of FIG. 6c which is a view of the shell component 15 in the direction B (representation at the top left in FIG. 6c) without the platform 11.

The shell section 35 (FIG. 6b) is provided with a recess 42 matched to the foot section 43 of the insert 33 (FIG. 6a) which has projections 46 which are aligned with the bores 44 of the foot section 43 and are deformed in the manner of rivets on the pressing for the fastening of the insert 33 to the shell section 35.

The multi-part design of the artificial joint component 15 with the joint section 35 consisting of plastic and the metallic insert 33 permits an advantageous metal-to-metal connection between the joint component 15 and the platform 11.

Figure 7:
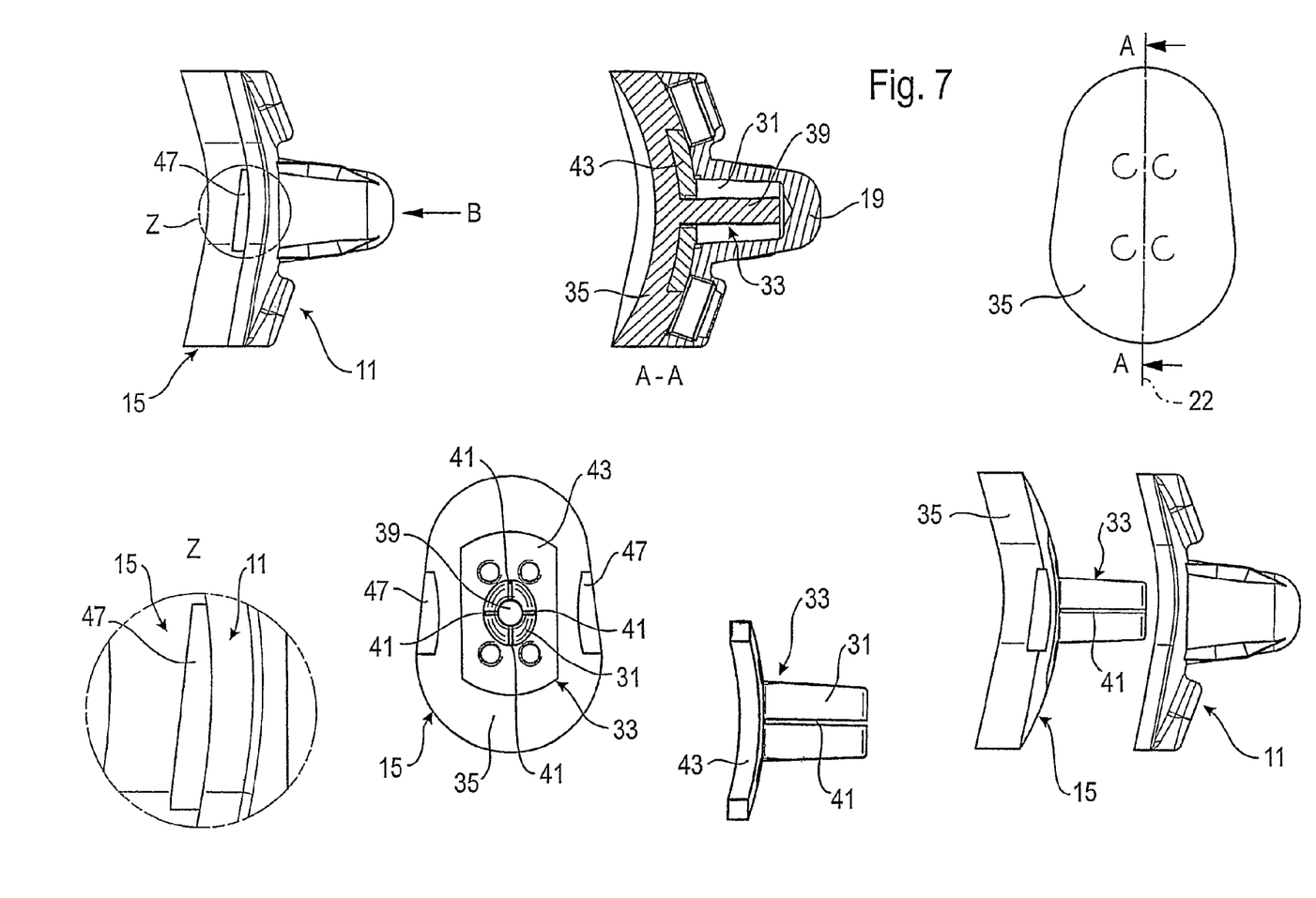
Figure 8:
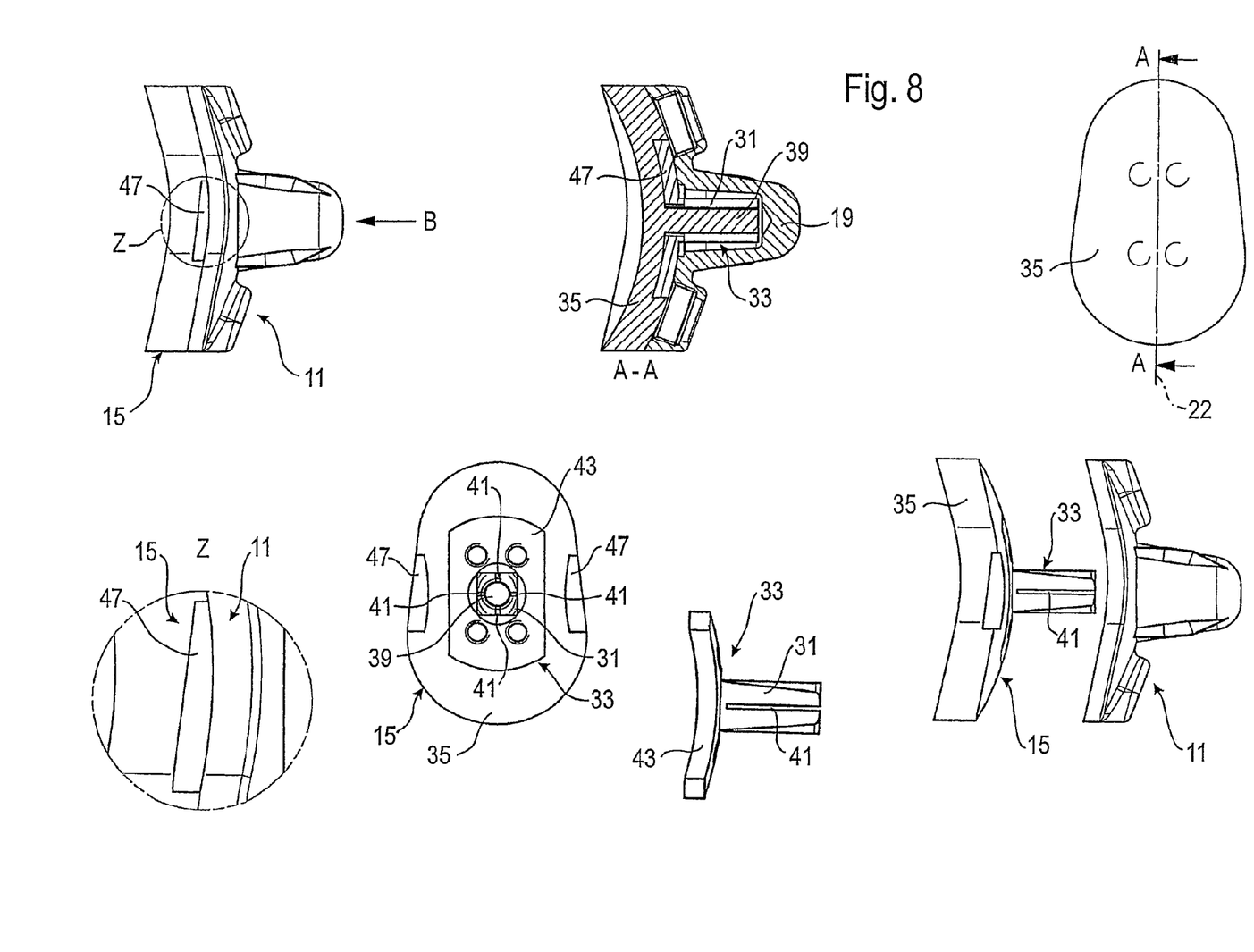

The embodiments of FIGS. 7 and 8 differ from that of FIGS. 6a-6c in each case only by the design of the conical pin 31 of the insert 33.

In the variant of FIG. 7, the fixing section 31 is in turn a complete cone which is, however, provided with longitudinal slots 41. Segments which are resilient independently of one another are hereby formed, whereby the demands on the manufacture tolerances for the conical inner side of the pin 19 of the platform 11 are reduced without the reliability of the press fit connection between the fixing section 31 and the pin 19 being impaired. The prolongation 39 of the shell section 35 can likewise be provided with longitudinal slots.

Starting from the foot section 43 of the insert 33, the fixing section 31 can be formed cylindrically over a specific length before it merges into a conical shape and tapers in the direction of its free end. It can hereby be achieved that the individual segments of the fixing section 31 defined by the longitudinal slots 41 are not deflected in the cylindrical region, but mainly in the region of the free end of the fixing section 31 and represent flexion springs in this respect.

Provision can be made in this variant for the internal thread of the insert 33 for the press-off instrument (cf. explanations on the embodiment of FIGS. 6a-6c) to be formed only within the cylindrical region of the fixing section 31.

In the variant of FIG. 8, the fixing section 31 is in turn provided with longitudinal slots 41, with this variant also being possible without longitudinal slots of this type.

The fixing section 31 is not made as a complete cone here, but has an outer cross-sectional shape which is inscribed in the inner cross-sectional shape of the pin 19 of the platform 11 and is made rectangular here. The press-fit connection is consequently not established by a full-areal contact between the fixing section 31 and the inner side of the pin 19, but via a plurality of linear or strip-like contact positions which are distributed discretely over the periphery. This variant can be manufactured even more simply due to the lower demands on the production tolerances.

Reference Numeral List 11 platform for glenoid
12 shaft
14 artificial joint socket for glenoid
14' artificial joint socket for humerus
14a screw
15 shell component for glenoid
16 artificial joint head for humerus
17 ball component for glenoid
19 pin
20 rib
21 screw mount
22 main plane
23 polyaxial anchoring screw
25 anchoring collar
27 fixing nut
29 head of the anchoring screw
31 fixing section
32 ring projection
33 fixing piece, insert
35 shell section
37 ball section
39 prolongation
41 longitudinal slot
42 recess
43 foot section
44 bore
45 internal thread
46 projection
47 release cut-out
49 anchorage projection
A shoulder blade (scapula)
B joint socket (glenoid)
C acromion
D coracoid
E upper arm bone (humerus)

What is claimed is:

1. An artificial joint assembly comprising:
an artificial joint component having a non-circular tapered protrusion extending therefrom, the non-circular tapered protrusion defining a protrusion axis and having, tapering along a total length of the non-circular tapered protrusion, one single continuous taper, the joint component comprising one of: i) a shell component adapted for an anatomical configuration of the joint assembly, and ii) a ball component adapted for an inverse configuration of the joint assembly; and a base platform having a hollow pin projecting from a convex side of the base platform including an internal wall defining a tapered internal cavity, the tapered internal cavity sized to receive the protrusion of the artificial joint component, wherein the base platform includes at least one screw mount, the at least one screw mount defining a passage extending from a concave side of the base platform to the convex side of the base platform, the at least one screw mount having an anchoring collar that projects from the convex side of the base platform, wherein a central axis of the anchoring collar coincides with a central axis of the at least one screw mount, the base platform adapted to be anchored to a bone by said hollow pin and the anchoring collar, the tapered protrusion of the artificial joint component cooperating with the tapered internal cavity of the hollow pin to axially fix the artificial joint component to the base platform with respect to the protrusion axis by taper locking, and at least a portion of the internal wall defining the cavity of the hollow pin having a non-circular inner cross-section, so that the internal wall defining the cavity of the hollow pin cooperates with the non-circular tapered protrusion of the artificial joint component to rotatably fix said artificial joint component to the base platform when the non-circular tapered protrusion is received in the internal cavity of the hollow pin, wherein the anchoring collar is positioned along a long axis of the cavity of the hollow pin, the long axis disposed along a common plane of the base platform.

2. The artificial joint assembly of claim 1, wherein the hollow pin has an outer side which tapers conically.

3. The artificial joint assembly of claim 1, wherein at least a portion of the hollow pin has a non-circular outer cross-section, wherein the base platform is adapted to be rotatably fixed to the bone.

4. The artificial joint assembly of claim 3, wherein the noncircular outer cross-section defines one of an oval and an ellipse.

5. The artificial joint assembly of claim 1, wherein the base platform includes at least two screw mounts that are configured to receive polyaxial anchoring screws, wherein the base platform is adapted to have a secondary anchorage in the bone.

6. The artificial joint assembly of claim 5, wherein a central axis of the hollow pin and a central axis of each of the at least two screw mounts are disposed in the common plane.

7. The artificial joint assembly of claim 6, wherein at least a portion of the hollow pin has an outer cross-sectional shape defining one of an oval and an ellipse, the hollow pin having a main axis which lies in the common plane.

8. The artificial joint assembly of claim 5, wherein central axes of the at least two of the screw mounts extend in different directions.

9. The artificial joint assembly of claim 1, wherein the inner cross-section of the pin has a profile which corresponds to a profile of an outer cross-section of the hollow pin.

10. The artificial joint assembly of claim 1, wherein the internal wall of the hollow pin and the outer wall of the protrusion define total peripheral contact when the protrusion is received in the internal cavity of the hollow pin.

11. The artificial joint assembly of claim 1, wherein the protrusion defines an elliptical outer cross-sectional shape.

12. The artificial joint assembly of claim 1, wherein the protrusion is arranged centrally with respect to the joint component, wherein the joint component is fixable to the base platform in two rotational orientations.

13. A system for an artificial joint, the system comprising:
a plurality of different artificial joint components, each of the joint components having a non-circular tapered protrusion extending therefrom, each protrusion having a single continuous taper along a total length of an external wall of the non-circular tapered protrusion;

a base platform having a non-circular shape and a hollow pin projecting form a convex side of the base platform including an internal wall defining a continuously tapered internal cavity, the internal cavity sized to receive the non-circular tapered protrusion of any of the artificial joint components, the base platform adapted to be anchored to a bone by the hollow pin, the external wall of any of the non-circular tapered protrusions cooperating with the internal wall of the hollow pin to axially fix a respective one of the artificial joint components to the base platform by taper locking when the non-circular tapered protrusion is received within the internal cavity of the pin, and at least a portion of the internal wall defining the cavity of the hollow pin having a non- circular inner cross-section, so that the internal wall defining the cavity of the hollow pin cooperates with said external wall of the non-circular tapered protrusion of any one of the artificial joint components to rotatably fix one of the artificial joint components to the base platform when the non-circular tapered protrusion is received in the internal cavity of the hollow pin, whereby cooperation of the single continuous taper of the external wall and the continuously tapered internal cavity operates to both axially fix and rotatably fix one of said plurality of artificial joint components to the base platform, wherein at least a first one of the artificial joint components defines an anatomical configuration when the first one of the artificial joint components is anchored to the base platform, wherein the first one of the artificial joint components is removable from the base platform and is exchangeable for at least a second one of the artificial joint components, and wherein the at least second one of the artificial joint components defines an inverse configuration when the at least second one of the artificial joint components is anchored to the base platform.

14. The modular kit of claim 13, wherein the base platform comprises screw mounts for polyaxial anchoring screws, and wherein the base platform is adapted to have a secondary anchorage in the bone.

15. An artificial joint assembly comprising:
an artificial joint component having a non-circular tapered protrusion extending therefrom, the non-circular tapered protrusion defining a protrusion axis and having a single continuous taper along a total length of the non-circular tapered protrusion, the joint component comprising one of: i) a shell component adapted for an anatomical configuration of the joint assembly, and ii) a ball component adapted for an inverse configuration of the joint assembly; and a base platform having a non-circular shape and a hollow pin projecting from a convex side of the base platform including an internal wall defining a tapered internal cavity, the tapered internal cavity sized to receive the non-circular tapered protrusion of the artificial joint component, wherein a width of the base platform decreases along a longitudinal axis of the base platform, wherein the base platform includes at least one screw mount, the at least one screw mount defining a passage extending from a concave side of the base platform to a convex side of the base platform, the at least one screw mount having an anchoring collar that projects from the convex side of the base platform, wherein a central axis of the anchoring collar coincides with a central axis of the at least one screw mount;

the tapered protrusion of the artificial joint component cooperating with the tapered internal cavity of the hollow pin to axially fix the artificial joint component to the base platform with respect to the protrusion axis by taper locking, and at least a portion of the internal wall defining the cavity of the hollow pin having a non-circular inner cross-section, so that the internal wall defining the cavity of the hollow pin cooperates with the non-circular tapered protrusion of the artificial joint component to rotatably fix said artificial joint component to the base platform when the non-circular tapered protrusion is received in the internal cavity of the hollow pin, wherein the anchoring collar is positioned along a long axis of the cavity of the hollow pin, the long axis disposed along the longitudinal axis of the base platform.

16. The artificial joint assembly of claim 15, wherein the non-circular protrusion is adapted to connect to the hollow pin with one of a clamping connection and a press fit connection.

17. The artificial joint assembly of claim 15, wherein the non-circular tapered protrusion of the artificial joint component comprises a conical press seat, so that the non-circular tapered protrusion is adapted to connect to the hollow pin with a self-locking press fit connection.

18. The artificial joint assembly of claim 15, wherein the protrusion is formed as a separate piece from the artificial joint component, the separate piece connected to the artificial joint component, so that the connection means comprises the separate piece.

19. The artificial joint assembly of claim 15, wherein the at least one screw mount is configured to receive a polyaxial anchoring screw, wherein the base platform is adapted to have a secondary anchorage in the bone.

* * * * *

UNITED STATES PATENT AND TRADEMARK OFFICE
CERTIFICATE OF CORRECTION

PATENT NO.      : 8,690,951 B2                                    Page 1 of 1
APPLICATION NO. : 12/093855
DATED           : April 8, 2014
INVENTOR(S)     : Baum et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 64 days.

Signed and Sealed this

Twenty-ninth Day of September, 2015

Michelle K. Lee
*Director of the United States Patent and Trademark Office*